(12) United States Patent
Takita et al.

(10) Patent No.: US 10,952,973 B2
(45) Date of Patent: Mar. 23, 2021

(54) PRODUCTION METHOD OF PREGABALIN-CONTAINING COMPOSITION AND PREGABALIN-CONTAINING COMPOSITION

(71) Applicant: NITTO DENKO CORPORATION, Ibaraki (JP)

(72) Inventors: Tomohito Takita, Ibaraki (JP); Kaiji Fujiwara, Ibaraki (JP); Chie Matsumoto, Ibaraki (JP); Akinori Sugiyama, Ibaraki (JP); Jyun Isayama, Tokyo (JP); Toshinari Honda, Tokyo (JP); Ai Funasaki, Tokyo (JP)

(73) Assignee: NITTO DENKO CORPORATION, Ibaraki (JP)

( * ) Notice: Subject to any disclaimer, the term of this patent is extended or adjusted under 35 U.S.C. 154(b) by 0 days.

(21) Appl. No.: 16/354,275

(22) Filed: Mar. 15, 2019

(65) Prior Publication Data
US 2019/0290596 A1 Sep. 26, 2019

(30) Foreign Application Priority Data
Mar. 22, 2018 (JP) .............................. JP2018-053905

(51) Int. Cl.
*A61K 9/70* (2006.01)
*A61P 25/08* (2006.01)
*A61K 9/00* (2006.01)
*A61K 31/385* (2006.01)

(52) U.S. Cl.
CPC .......... *A61K 9/7023* (2013.01); *A61K 9/0014* (2013.01); *A61K 31/385* (2013.01); *A61P 25/08* (2018.01)

(58) Field of Classification Search
CPC combination set(s) only.
See application file for complete search history.

(56) References Cited

U.S. PATENT DOCUMENTS

| 6,197,819 B1 * | 3/2001 | Silverman ............ A61K 31/197 514/561 |
| 2008/0014280 A1 | 1/2008 | Kumar et al. |
| 2016/0256422 A1 | 9/2016 | Shudo et al. |

FOREIGN PATENT DOCUMENTS

| JP | H06-006534 B2 | 1/1994 | |
| WO | WO-2010150221 A1 * | 12/2010 | ........... A61K 9/0056 |
| WO | WO 2013/015578 A1 | 1/2013 | |
| WO | WO 2013/114283 A1 | 8/2013 | |
| WO | WO 2014/112152 A1 | 7/2014 | |

OTHER PUBLICATIONS

Strauss et al. Pathology Oncology Research, (2002), 8(1), p. 47-53.*
Prausnitz et al., Nat Biotechnol., (2008), 26(11), p. 1261-1268.*
European Patent Office, Extended European Search Report in European Patent Application No. 19163239.7 (dated Jul. 3, 2019).

* cited by examiner

*Primary Examiner* — Kortney L. Klinkel
*Assistant Examiner* — Tori Strong
(74) *Attorney, Agent, or Firm* — Leydig, Voit & Mayer, Ltd.

(57) ABSTRACT

Provided are a production method of a pregabalin-containing composition, which suppresses crystallization of pregabalin, and a pregabalin-containing composition that shows suppressed crystallization of Pregabalin. The production method of the pregabalin-containing composition of the present invention contains steps of:
(1) dissolving pregabalin in an aqueous solution of an acid to prepare an aqueous solution of a salt of pregabalin; (2) mixing the aqueous solution of pregabalin salt and a hydrophilic resin to prepare a mixture thereof; and (3) concentrating the mixture; wherein the acid has an acid dissociation constant lower than that of pregabalin.

20 Claims, 3 Drawing Sheets

PRODUCTION METHOD OF PREGABALIN-CONTAINING COMPOSITION AND PREGABALIN-CONTAINING COMPOSITION

TECHNICAL FIELD OF THE INVENTION

The present invention relates to a production method of a pregabalin-containing composition and pregabalin-containing composition.

BACKGROUND OF THE INVENTION

Pregabalin is a medicament used for mitigating pain and is commercially available as an oral drug. However, a treatment of pain by oral administration, which is a systemic administration, requires administration of high doses and continuous administration. This in turn gives rise to a serious problem of side effects such as drowsiness, dizziness, edema, rash, and blurred vision. For this reason, a method other than oral administration such as transdermal administration has been considered for the treatment with pregabalin (patent document 1).

In transdermal administration, the stratum corneum layer, which constitutes the outermost surface of the skin, has a barrier function to prevent invasion of foreign substances into the body, and has high hydrophobicity. It is therefore considered difficult for a medicament having high hydrophilicity such as pregabalin to permeate through the stratum corneum layer.

On the other hand, a method for enhancing skin permeability of a medicament in transdermal administration is also known. For example, a method for increasing the amount of a medicament that permeates through the stratum corneum (permeability) is known, which includes raising the concentration of the medicament contained in a drug-containing layer of a transdermal agent to a supersaturated state (patent document 2).

DOCUMENT LIST

Patent Documents

[patent document 1] WO2014/112152
[patent document 2] JP-B-6-006534

SUMMARY OF THE INVENTION

Problems to be Solved by the Invention

However, when the concentration of a medicament contained in a drug-containing layer is raised, the stability of the medicament in the drug-containing layer is degraded. As a result, even a small stimulation causes crystallization of the medicament, and the crystallization causes a problem of decreased permeability of the medicament.

The present invention aims to solve the aforementioned problem. That is, the present invention aims to provide a production method of a pregabalin-containing composition, which suppresses crystallization of pregabalin, and the aforementioned pregabalin-containing composition.

Means of Solving the Problems

The present invention provides, for example, the following [1] to [7].

[1] A method for producing a pregabalin-containing composition, comprising steps of:
(1) dissolving pregabalin in an aqueous solution of an acid to prepare an aqueous solution of a salt of pregabalin;
(2) mixing the aforementioned aqueous solution of pregabalin salt and a hydrophilic resin to prepare a mixture thereof; and
(3) concentrating the aforementioned mixture;
wherein the aforementioned acid has an acid dissociation constant lower than that of pregabalin.

[2] The production method of the aforementioned [1], wherein the aforementioned acid is an inorganic acid.

[3] The production method of the aforementioned [1] or [2], wherein a content of the hydrophilic resin is 0.5-50 parts by mass per 100 parts by mass of the salt contained in the aforementioned mixture.

[4] A pregabalin-containing composition comprising a salt of pregabalin with an acid, and a hydrophilic resin, wherein the aforementioned acid has an acid dissociation constant lower than that of pregabalin.

[5] The pregabalin-containing composition of the aforementioned [4], wherein a content of the hydrophilic resin is 0.5-50 parts by mass per 100 parts by mass of the salt contained in the aforementioned pregabalin-containing composition.

[6] The production method of any of the aforementioned [1]-[3] or the pregabalin-containing composition of the aforementioned [4] or [5], wherein the acid has a pKa of not more than 4, and the hydrophilic resin is dissolved at not less than 20 g/l in water at 20° C.

[7] The production method of any of the aforementioned [1]-[3] or the pregabalin-containing composition of the aforementioned [4] or [5], wherein the acid is selected from the group consisting of phytic acid, acrylic acid, polyacrylic acid, poly(p-styrene sulfonic acid), polyvinyl sulfonic acid, polyacrylamide sulfonic acid, alkylsulfuric acid, lactic acid, hydrochloric acid, nitric acid, phosphoric acid, sulfuric acid, hydrobromic acid, hydroiodic acid and heparin, and the hydrophilic resin is selected from the group consisting of polyvinyl acetate, polyvinylpyrrolidone, polyethylene glycol, polyvinyl alcohol, cellulose, cellulose ester, carrageenan, polyacrylic acid, polymethacrylic acid, starch, gelatin, heparin, polyvinyl sulfonic acid, polyacrylamide and polyacrylamide sulfonic acid.

Effect of the Invention

According to the production method of the pregabalin-containing composition of the present invention, a pregabalin-containing composition that shows suppressed crystallization of pregabalin can be produced.

In addition, according to the pregabalin-containing composition of the present invention, crystallization of pregabalin is suppressed and superior storage stability can be achieved.

DESCRIPTION OF EMBODIMENTS

Figure 1:
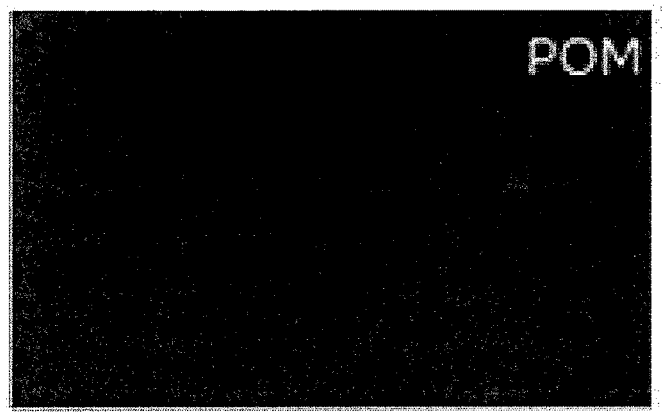
FIG. 1 is a polarization microscope photograph showing the state of the pregabalin-containing composition obtained in Example 1.

The mode of embodiment of the present invention is explained below.

Unless otherwise indicated, each chemical substance exemplified in the present specification, for example, chemical substances used in each step of the production method of the pregabalin-containing composition of the present invention, and chemical substances constituting the pregabalin-containing composition of the present invention may be used singly or in combination of two or more kinds thereof.

By going through step (1), pregabalin is acid-treated and a salt of pregabalin, specifically, conjugated acid, can be formed.

The reason for forming a salt of pregabalin (conjugated acid) in step (1) is explained below.

A compound used as a medicament (particularly transdermal drug) is preferably used in an amorphous state, namely, as an amorphous compound, since it is more easily taken into the body.

To obtain a composition containing pregabalin in an amorphous form, it is necessary to destroy pregabalin crystal. Being a zwitter ion compound, pregabalin is ionically bonded to each other to form an ionic crystal. Pregabalin crystal has a melting point of 190-200° C. and it is difficult to break pregabalin crystal by heating.

On the other hand, pregabalin as a zwitter ion compound is in an equilibrium state shown by the following formula (1) in water. In this equilibrium state, the ionic bond between pregabalin is considered to be eliminated by moving the equilibrium to a state (shown by the following formula (1)(a)) that is not zwitterion (the following formula (1)(b)), as a result of which pregabalin crystal can be destroyed.

The state of the following formula (1)(a) shows a conjugated acid of the zwitter ion (the following formula (1)(b)). The carboxyl group of pregabalin has an acid dissociation constant (pKa) of about 4.2. Thus, when pregabalin is dissolved in an aqueous solution of an acid having pKa lower than 4.2 in step (1), a conjugated acid (the following formula (1)(a)) is formed and pregabalin crystal can be destroyed.

formula (1)

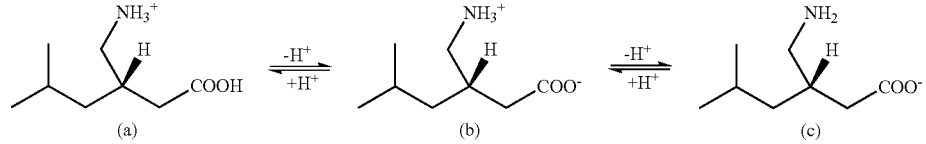

<Production Method Of Pregabalin-Containing Composition>

The production method of the pregabalin-containing composition of the present invention includes steps of:
(1) dissolving pregabalin in an aqueous solution of an acid (hereinafter to be also referred to as "acid aqueous solution") to prepare an aqueous solution of a salt of pregabalin (hereinafter to be also referred to as "pregabalin salt aqueous solution");
(2) mixing the aforementioned aqueous solution of pregabalin salt and a hydrophilic resin to prepare a mixture thereof; and
(3) concentrating the aforementioned mixture.

The pregabalin-containing composition obtained by the production method of the pregabalin-containing composition of the present invention is preferably used as a transdermal agent. Specifically, it is used for a transdermal agent containing a drug-containing layer as a constituent material of the drug-containing layer.

<Step (1)>

In step (1), pregabalin is dissolved in an acid aqueous solution to give a pregabalin salt aqueous solution.

In step (1), as the acid aqueous solution, an aqueous solution of an acid having an acid dissociation constant (hereinafter to be also simply referred to as "pKa") lower than that of pregabalin is used.

As a state that is not zwitterion, the above-mentioned formula (1)(c), specifically, conjugated base of zwitter ion, can also be mentioned. However, to achieve a conjugate base state of pregabalin, it is necessary to treat pregabalin with a base, and bases generally melt protein. From the aspects of the constitution and use of the obtained pregabalin-containing composition, a treatment using a base is not appropriate. For this reason, in the production method of the pregabalin-containing composition of the present invention, a treatment with an acid is performed to form a conjugated acid.

An acid constituting the acid aqueous solution has a pKa lower than that of Pregabalin. Using an acid having a lower pKa for the acid aqueous solution, the equilibrium of pregabalin can be sufficiently moved to a conjugated acid side. For this end, the pKa of the acid is preferably lower by at least one, more preferably at least two, than the pKa of pregabalin. More specifically, the pKa of the acid is preferably not more than 4, more preferably not more than 3, further preferably not more than 2.

The pKa of the acid aqueous solution is preferably not more than 3, more preferably not more than 2.

In the present specification, the pKa of the acid aqueous solution is the value at 23° C., acid concentration 6 mol/L or 0.35 mol/L.

The molecular weight of the acid used for the acid aqueous solution is preferably low. When excessive amount of acid (acid that did not contribute to the formation of salt of pregabalin) is removed by concentrating the mixture in step (3), an acid with a low molecular weight tends to volatilize well and is easily removed.

When a pregabalin-containing composition is used as a transdermal agent, the medicament (pregabalin) advantageously shows higher skin permeability when the acid constituting the acid aqueous solution has a lower molecular weight. For specific explanation, pregabalin is contained as a salt in the pregabalin-containing composition, and when the acid has a high molecular weight, the content ratio (mass standard) of pregabalin in the pregabalin-containing composition decreases. When the pregabalin-containing composition is used as a transdermal agent, therefore, the content ratio (concentration) of the medicament in the drug-containing layer (pregabalin-containing composition) of the transdermal agent can be increased by reducing the molecular weight of the acid constituting the acid aqueous solution. As a result, the skin permeability of the medicament can be enhanced.

To be specific, the molecular weight of the acid constituting the acid aqueous solution is generally not more than 5,000, preferably not more than 1,000, further preferably 20-700.

Examples of the acid used for the acid aqueous solution include organic acids such as phytic acid, acrylic acid, polyacrylic acid, poly(p-styrene sulfonic acid), polyvinyl sulfonic acid, polyacrylamide sulfonic acid, alkylsulfuric acid (dodecylsulfuric acid etc.), and lactic acid; inorganic acids such as hydrochloric acid, nitric acid, phosphoric acid, sulfuric acid, hydrobromic acid, and hydroiodic acid; and heparin.

Among these, inorganic acids are preferable since they can lower the pKa of the acid aqueous solution and reduce the 10 molecular weight thereof.

The content of the acid in the acid aqueous solution is generally 1-12 mol/L, preferably 2-8 mol/L.

The amount of the acid aqueous solution to be used is generally an amount that makes the amount of the acid in the acid aqueous solution 0.1-5 molar equivalents, preferably 0.5-3 molar equivalents, relative to pregabalin.

Pregabalin is generally dissolved in an acid aqueous solution at 0-80° C., preferably 10-40° C.

For dissolution, for example, a stirring means such as a mixer, an ultrasonic wave, a mix rotor and a magnetic stirrer can be used.

In step (1), after dissolving pregabalin in an acid aqueous solution, for example, acid aqueous solution of pregabalin may be concentrated by a drying means such as air drying, drying by heating, freeze drying and vacuum drying.

The concentration operation in step (3) can be easily performed by concentrating the acid aqueous solution of pregabalin.

In step (1), a pregabalin salt aqueous solution can be obtained by the above operation.
<Step (2)>

In step (2), the aforementioned pregabalin salt aqueous solution and a hydrophilic resin are mixed to prepare a mixture.

In the pregabalin salt aqueous solution obtained in step (1), pregabalin is in equilibrium. The equilibrium is moved to zwitterion (the aforementioned formula (1)(b)) by stimulation of heat, volatilization of acid and the like, and crystallization of pregabalin proceeds.

That is, a pregabalin salt aqueous solution is mixed with a hydrophilic resin considered to fix the equilibrium of pregabalin to the state of conjugated acid (the aforementioned formula (1)(a)) and/or prevent formation of ion crystal of pregabalin even when the equilibrium of pregabalin is moved to zwitterion by the aforementioned stimulation. Since pregabalin salt is hydrophilic, it is mixed well with a hydrophilic resin.

The hydrophilic resin only needs to have hydrophilicity permitting mixing with a hydrophilic pregabalin salt, and generally refers to a resin that is dissolved at not less than 20 g/l, preferably not less than 100 g/l, in water at 20° C.

Specific examples of the hydrophilic resin include polyvinyl acetate, polyvinylpyrrolidone, polyethylene glycol, polyvinyl alcohol, cellulose, cellulose ester, carrageenan, polyacrylic acid, polymethacrylic acid, starch, gelatin, heparin, polyvinyl sulfonic acid, polyacrylamide, and polyacrylamide sulfonic acid.

The weight average molecular weight of hydrophilic resin is generally 1,000-500,000, preferably 10,000-360,000, based on polystyrene.

When the molecular weight of the hydrophilic resin falls within the above-mentioned range, the concentration of pregabalin in the pregabalin-containing composition can be increased, and crystallization of pregabalin in the Pregabalin-containing composition can be suppressed.

The viscosity of a hydrophilic resin aqueous solution with a concentration of 5 mass % according to JIS Z 8803 is generally 5-1,000 mPa·s, preferably 10-200 mPa·s.

When the viscosity of the hydrophilic resin (hydrophilic resin aqueous solution) falls within the above-mentioned range, crystallization of pregabalin in the pregabalin-containing composition can be suppressed.

The amount of the hydrophilic resin to be used is generally an amount that makes the content of the hydrophilic resin 0.1-100 parts by mass, preferably 0.5-50 parts by 15 mass, more preferably 1-30 parts by mass, relative to 100 parts by mass of the salt in the mixture.

When the amount of the hydrophilic resin to be used falls within the above-mentioned range, a pregabalin-containing composition suppressing crystallization of pregabalin and having a high content ratio (mass standard) of pregabalin in the pregabalin-containing composition can be produced.

A pregabalin salt aqueous solution and a hydrophilic resin are generally mixed at 0-80° C., preferably 10-40° C.

For mixing, for example, a mixer, an ultrasonic wave, a mix rotor or a magnetic stirrer can be used.

It is preferable to perform step (2) within 48 hr from completion of step (1).

In step (2), a mixture containing a pregabalin salt and a hydrophilic resin can be obtained by the above operation.
<Step (3)>

In step (3), the aforementioned mixture is concentrated.

By going through step (3), water and a part of the acid constituting the acid aqueous solution used in step (1) and not contributing to the formation of a pregabalin salt are removed from the mixture. In the concentrated mixture, the content ratio of water is generally not more than 10 mass %, preferably not more than 5 mass %. The content ratio of the acid is generally not more than 5 mass %, preferably not more than 2 mass %.

By removing water and the acid, the aforementioned function of the hydrophilic resin (to fix the equilibrium of pregabalin to the state of conjugated acid (the aforementioned formula (1)(a)) and/or prevent formation of ion crystal of pregabalin even when the equilibrium of pregabalin is moved to zwitterion by the aforementioned stimulation) is sufficiently expressed. As a result, a pregabalin-containing composition having a high content ratio (mass standard) of pregabalin and suppressing crystallization of Pregabalin can be produced.

Examples of a method for concentrating the mixture include air drying, drying by heating, freeze drying and vacuum drying. Among these, air drying is preferable since decomposition or deterioration of pregabalin due to drying can be prevented.

In step (3), after concentrating the mixture, components generally used for a drug-containing layer of a transdermal agent can be added as necessary.

Specific examples of the components generally used for a drug-containing layer of a transdermal agent include the excipient, lubricant, binder, disintegrant, thickener, suspending agent, emulsifier, isotonicity agent, buffering agent, soothing agent, stabilizer, preservative, pH adjuster, algefacient, antioxidant, and moistening agent described in WO 2006/064906.

By the above operation, a pregabalin-containing composition as a production object in step (3) can be obtained. That is, a pregabalin-containing composition can be produced by performing step (1), step (2) and step (3) in this order.

According to the production method of the pregabalin-containing composition of the present invention having step (1), step (2) and step (3), a pregabalin-containing composition sufficiently suppressing crystallization of Pregabalin can be obtained. Even when a composition containing pregabalin at a high content ratio is stimulated with heat or the like, superior storage stability can be achieved regardless of the storage environment conditions since crystallization of pregabalin is suppressed.

<Pregabalin-Containing Composition>

The pregabalin-containing composition of the present invention contains a salt of pregabalin with an acid having a dissociation constant (pKa) lower than that of pregabalin and a hydrophilic resin.

Specific examples of the acid (acid having a dissociation constant (pKa) lower than that of pregabalin) relating to the salt of pregabalin and constituting the pregabalin-containing composition of the present invention, and specific examples of the hydrophilic resin include those exemplified in the aforementioned "the production method of the pregabalin-containing composition".

In the pregabalin-containing composition of the present invention, the content of the aforementioned hydrophilic resin per 100 parts by mass of the aforementioned salt is generally 0.1-100 parts by mass, preferably 0.5-50 parts by mass, more preferably 1-30 parts by mass.

When the ratio of the hydrophilic resin falls within the above-mentioned range, a pregabalin-containing composition suppressing crystallization of pregabalin and having a high content ratio (mass standard) of pregabalin can be produced.

The pregabalin-containing composition of the present invention can contain, as necessary, optional components, specifically, components generally used for a drug-containing layer of a transdermal agent.

Specific examples of the components generally used for a drug-containing layer of a transdermal agent include those exemplified in the aforementioned "the production method of the pregabalin-containing composition".

The pregabalin-containing composition of the present invention can be produced, for example, by the production method of the pregabalin-containing composition of the present invention.

Such pregabalin-containing composition of the present invention shows sufficiently suppressed crystallization of pregabalin since pregabalin is contained as a salt with a particular acid together with a hydrophilic resin. Even when a composition containing pregabalin at a high content ratio is stimulated with heat or the like, superior storage stability can be achieved regardless of the storage environment conditions since crystallization of pregabalin is suppressed.

The pregabalin-containing composition of the present invention as described above suppresses crystallization of Pregabalin and is superior in storage stability even though the content ratio of pregabalin is high. Thus, it is useful as a material for forming a drug-containing layer of a transdermal agent containing pregabalin as the principal active ingredient.

EXAMPLES

The present invention is explained in detail in the following by referring to Examples, which are not to be construed as limitative.

Comparative Example 1

Pregabalin was dissolved at 6 mol/L hydrochloric acid aqueous solution (pKa=−3.7 (23° C.), used in an amount achieving 1 molar equivalent of hydrochloric acid relative to pregabalin) to give an aqueous solution containing pregabalin hydrochloride at 49 mass %. The aforementioned aqueous solution (0.2 ml) was placed on a glass slide and dried at 23° C. for 24 hr to produce a pregabalin-containing composition (content ratio of pregabalin 81 mass %) of Comparative Example 1.

The pregabalin-containing composition of Comparative Example 1 was observed under a polarization microscope to find no crystal of Pregabalin. Thus, a pregabalin-containing composition free of crystallization of pregabalin was obtained by the aforementioned production method, even though pregabalin was contained at a high concentration.

The pregabalin-containing composition of Comparative Example 1 was further stored at 23° C. for 48 hr, and the state of the pregabalin-containing composition was observed under a polarization microscope. As a result, partially crystallized pregabalin was confirmed. The results thereof are shown in the following Table 1.

Example 1

The pregabalin-containing composition of Comparative Example 1 was dissolved in water at 23° C. to adjust pregabalin hydrochloride in the pregabalin salt aqueous solution to 10 mass %. To the obtained pregabalin salt aqueous solution was added at 23° C. polyvinylpyrrolidone (weight average molecular weight based on polystyrene 40,000) in an amount that made pregabalin hydrochloride:polyvinylpyrrolidone=4:1 (mass ratio) and they were mixed to give a mixture. Thereafter, the aforementioned mixture (0.2 ml) was placed on a glass slide and dried at 23° C. for 24 hr to produce a pregabalin-containing composition (content ratio of pregabalin 64 mass %) of Example 1.

The state of the obtained pregabalin-containing composition of Example 1 was observed under a polarization microscope in the same manner as in Comparative Example 1. Furthermore, the pregabalin-containing composition of Example 1 was further stored at 23° C. for 48 hr, and the state of the pregabalin-containing composition was observed under a polarization microscope to confirm the presence or absence of crystal. The results thereof are shown in the following Table 1.

Example 2

In the same manner as in Example 1 except that polyvinylpyrrolidone was added in an amount that made pregabalin hydrochloride:polyvinylpyrrolidone=9:1 (mass ratio) in the aforementioned Example 1 and they were mixed to give a mixture, a pregabalin-containing composition (content ratio of pregabalin 72 mass %) of Example 2 was produced.

The state of the obtained pregabalin-containing composition of Example 2 was observed under a polarization microscope in the same manner as in Comparative Example 1. Furthermore, the pregabalin-containing composition of Example 2 was further stored at 23° C. for 48 hr in the same manner as in Comparative Example 1, and the state of the pregabalin-containing composition was observed under a polarization microscope. The results thereof are shown in the following Table 1.

Comparative Example 2

Pregabalin was dissolved in water to achieve a content ratio of pregabalin of 10 mass %. Then, polyvinylpyrrolidone (weight average molecular weight based on polystyrene 40,000) in an amount that made pregabalin:polyvinylpyrrolidone=9:1 (mass ratio) was added and they were mixed to give a mixture. Thereafter, the aforementioned mixture (0.2 ml) was placed on a glass slide and dried at 23° C. for 24 hr to produce a pregabalin-containing composition (content ratio of pregabalin 90 mass %) of Comparative Example 2.

The state of the obtained pregabalin-containing composition of Comparative Example 2 was observed under a polarization microscope in the same manner as in Comparative Example 1. The results thereof are shown in the following Table 1.

Comparative Example 3

Pregabalin was dissolved in water to achieve a content ratio of pregabalin of 10 mass %. Then, polyacrylic acid (weight average molecular weight based on polystyrene 5,000) in an amount that made pregabalin:polyacrylic acid=1:1 (mass ratio) was added and they were mixed to give a mixture. Thereafter, the aforementioned mixture (0.2 ml) was placed on a glass slide and dried at 23° C. for 24 hr to produce a pregabalin-containing composition (content ratio of pregabalin 50 mass %) of Comparative Example 3.

The state of the obtained pregabalin-containing composition of Comparative Example 3 was observed under a polarization microscope in the same manner as in Comparative Example 1. The results thereof are shown in the following Table 1.

Comparative Example 4

Pregabalin was dissolved in water to achieve a content ratio of pregabalin of 10 mass %. Then, heparin (product name "Heparin sodium salt, from porcine intestinal mucosa", manufactured by Alfa Aesar) in an amount that made pregabalin:heparin=1:2 (mass ratio) was added and they were mixed to give a mixture. Thereafter, the aforementioned mixture (0.2 ml) was placed on a glass slide and dried at 23° C. for 24 hr to produce a pregabalin-containing composition (content ratio of pregabalin 33 mass %) of Comparative Example 4.

The state of the pregabalin-containing composition of Comparative Example 4 was observed under a polarization microscope in the same manner as in Comparative Example 1. The results thereof are shown in the following Table 1.

Comparative Example 5

Pregabalin was dissolved in water to achieve a content ratio of pregabalin of 10 mass %. Then, poly(p-styrene sulfonic acid) (product name "20% poly(p-styrene sulfonic acid) solution", manufactured by Wako Pure Chemical Industries, Ltd.) in an amount that made pregabalin:poly(p-styrene sulfonic acid)=2:1 (mass ratio) was added and they were mixed to give a 25 mixture. Thereafter, the aforementioned mixture (0.2 ml) was placed on a glass slide and dried at 23° C. for 24 hr to produce a pregabalin-containing composition (content ratio of pregabalin 67 mass %) of Comparative Example 5.

The state of the pregabalin-containing composition of Comparative Example 5 was observed under a polarization microscope in the same manner as in Comparative Example 1. The results thereof are shown in the following Table 1.

Comparative Example 6

Pregabalin was dissolved in water to achieve a content ratio of pregabalin of 10 mass %. Then, polyacrylic acid (product name "polyacryl acid 5000", manufactured by Wako Pure Chemical Industries, Ltd.) in an amount that made pregabalin:polyacrylic acid=1:1 (mass ratio) was added and they were mixed to give a mixture. Thereafter, the aforementioned mixture (0.2 ml) was placed on a glass slide and dried at 23° C. for 24 hr to produce a pregabalin-containing composition (content ratio of pregabalin 50 mass %) of Comparative Example 6.

The state of the obtained pregabalin-containing composition of Comparative Example 6 was observed under a polarization microscope in the same manner as in Comparative Example 1. The results thereof are shown in the following Table 1.

TABLE 1

Figure 2:
FIG. 2 is a polarization microscope photograph showing the state of the pregabalin-containing composition obtained in Example 2.

| | state of pregabalin-containing composition immediately after production | | state of pregabalin-containing composition after storage at 23° C. for 48 hr | | |
|---|---|---|---|---|---|
| | presence or absence of crystal | polarization microscope photograph | presence or absence of crystal | polarization microscope photograph | pregabalin content ratio |
| Example 1 | absent | — | absent | see FIG. 1 | 64 mass % |
| Example 2 | absent | — | absent | see FIG. 2 | 72 mass % |

TABLE 1-continued

Figure 3:
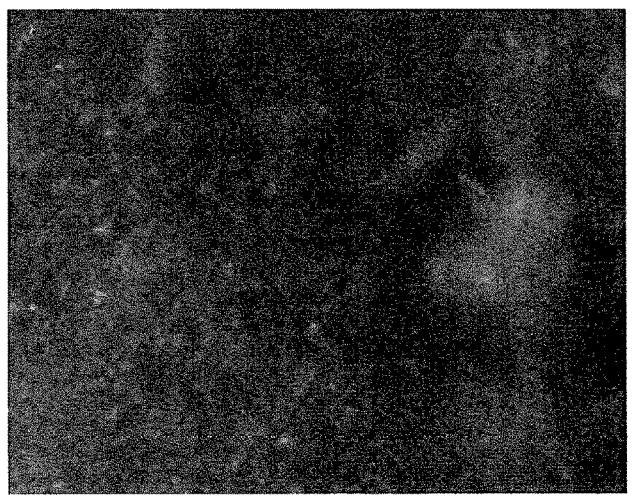
FIG. 3 is a polarization microscope photograph showing the state of the pregabalin-containing composition for comparison obtained in Comparative Example 2.
Figure 4:
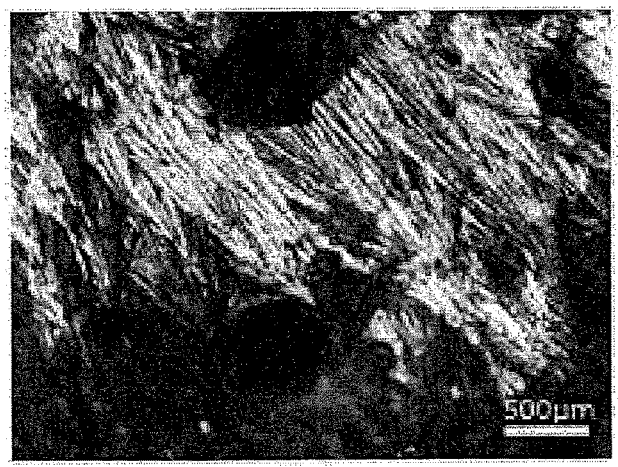
FIG. 4 is a polarization microscope photograph showing the state of the pregabalin-containing composition for comparison obtained in Comparative Example 3.
Figure 5:
FIG. 5 is a polarization microscope photograph showing the state of the pregabalin-containing composition for comparison obtained in Comparative Example 4.
Figure 6:
FIG. 6 is a polarization microscope photograph showing the state of the pregabalin-containing composition for comparison obtained in Comparative Example 5.
Figure 7:
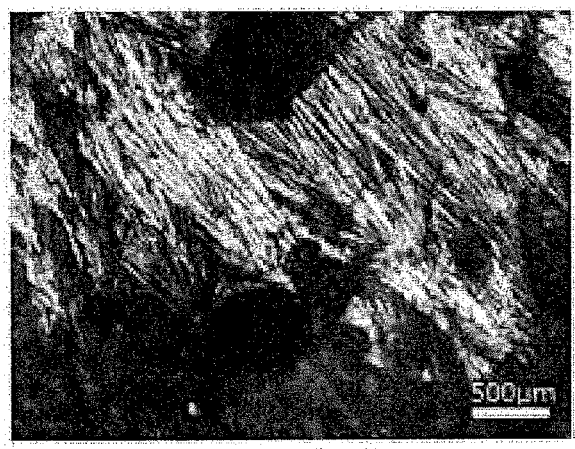
FIG. 7 is a polarization microscope photograph showing the state of the pregabalin-containing composition for comparison obtained in Comparative Example 6.

|  | state of pregabalin-containing composition immediately after production | | state of pregabalin-containing composition after storage at 23° C. for 48 hr | | |
| --- | --- | --- | --- | --- | --- |
|  | presence or absence of crystal | polarization microscope photograph | presence or absence of crystal | polarization microscope photograph | pregabalin content ratio |
| Comparative Example 1 | absent | — | present | — | 81 mass % |
| Comparative Example 2 | present | see FIG. 3 | unevaluated *[1] | — | 90 mass % |
| Comparative Example 3 | present | see FIG. 4 | unevaluated *[1] | — | 50 mass % |
| Comparative Example 4 | present | see FIG. 5 | unevaluated *[1] | — | 33 mass % |
| Comparative Example 5 | present | see FIG. 6 | unevaluated *[1] | — | 67 mass % |
| Comparative Example 6 | present | see FIG. 7 | unevaluated *[1] | — | 50 mass % |

*[1] Pregabalin-containing composition immediately after production contained crystal and evaluation after storage was not performed.

From the above results, it was confirmed that pregabalin-containing compositions suppressing crystallization of pregabalin could be obtained in Example 1 and Example 2 relating to the present invention, and the obtained pregabalin-containing compositions afforded superior storage stability suppressing crystallization of pregabalin even though they contained pregabalin at a high content ratio of not less than 60 mass %.

Example 3

Pregabalin was dissolved at 0.35 mol/L dodecylsulfuric acid aqueous solution (pKa=−3 (23° C.), used in an amount achieving 1 molar equivalent of dodecylsulfuric acid relative to pregabalin) to give an aqueous solution containing pregabalin dodecylsulfate at 15 mass %. The aforementioned aqueous solution (0.2 ml) was placed on a glass slide and dried at 23° C. for 24 hr to produce a pregabalin-containing composition (content ratio of pregabalin 38 mass %).

To the aforementioned pregabalin-containing composition was added polyvinylpyrrolidone (weight average molecular weight based on polystyrene 40,000) in an amount that made pregabalin dodecylsulfate:polyvinylpyrrolidone=8:2 (mass ratio), methanol was further added and they were mixed to give a mixture. Thereafter, the aforementioned mixture (1.4 ml) was dropped on an aluminum petri dish and dried at 23° C. for 24 hr to produce a pregabalin-containing composition (content ratio of pregabalin 30 mass %) of Example 3.

The state of the obtained pregabalin-containing composition of Example 3 was observed under a polarization microscope in the same manner as in Comparative Example 1. The results thereof are shown in the following Table 2. The obtained pregabalin-containing composition of Example 3 was prepared to have a thickness of 200 μm to give a Pregabalin-containing preparation of Example 3.

Comparative Example 7

To pregabalin was added at 23° C. polyvinylpyrrolidone (weight average molecular weight based on polystyrene 40,000) in an amount that made pregabalin:polyvinylpyrrolidone=8:2 (mass ratio), methanol was further added and they were mixed to give a mixture. Thereafter, the aforementioned mixture (1.5 ml) was dropped on an aluminum petri dish and dried at 23° C. for 24 hr to produce a pregabalin-containing composition (content ratio of pregabalin 80 mass %) of Comparative Example 7.

The state of the obtained pregabalin-containing composition of Comparative Example 7 was observed under a polarization microscope in the same manner as in Comparative Example 1. The results thereof are shown in the following Table 2. The obtained pregabalin-containing composition of Comparative Example 7 was prepared to have a thickness of 200 μm to give a Pregabalin-containing preparation of Comparative Example 7.

(Permeability Test)

The Pregabalin-containing preparations of Example 3 and Comparative Example 7 were each punched out in 6 mmϕ, and the obtained preparations were each attached to the stratum corneum layer side of the skin (intact skin) isolated from the abdomen of a hairless mouse, and fixed by applying a cover tape (medical tape manufactured by 3 M: 1774 W) over the aforementioned preparation. The isolated skin with the aforementioned preparation adhered and fixed thereonto was set on a flow-through diffusion cell apparatus, a receptor solution was sampled at given time intervals, and the skin permeation amount of pregabalin after 24 hr was calculated. As the receptor solution, phosphate buffered saline at 32° C. was used and the flow was about 2.5 mL/h. The concentration of pregabalin in the receptor solution was quantified by liquid chromatography—tandem mass spectrometry method (LCMSMS) using "ACQUITY TQD" (manufactured by Waters) and according to "Validation of Pregabalin in Human Plasma by LCMS Method", G. Uma, M. Manimala, M. Vasudevan, S. Karpagam and Deecaraman; International Journal of Research and Development in Pharmacy and Life sciences, 2012, Vol. 1, No. 3, 151-155 and the like. The results thereof are shown in the following Table 3.

TABLE 2

Figure 8:
FIG. 8 is a polarization microscope photograph showing the state of the pregabalin-containing composition obtained in Example 3.
Figure 9:
FIG. 9 is a polarization microscope photograph showing the state of the pregabalin-containing composition for comparison obtained in Comparative Example 7.

|  | state of pregabalin-containing composition immediately after production | state of pregabalin-containing composition after storage at 40° C., 75% RH for 1 week | |
| --- | --- | --- | --- |
|  | presence or absence of crystal | presence or absence of crystal | polarization microscope photograph |
| Example 3 | absent | absent | see FIG. 8 |
| Comparative Example 7 | present | present | see FIG. 9 |

TABLE 3

| | accumulated permeation amount ($\mu g/cm^2/24\ h$) |
|---|---|
| Example 3 | 4192 |
| Comparative Example 7 | ND |

From the above results, it was confirmed that pregabalin-containing composition suppressing crystallization of pregabalin could be obtained in Example 3 relating to the present invention, and superior storage stability suppressing crystallization of pregabalin could be obtained. Furthermore, it was confirmed that a pregabalin-containing preparation suppressing crystallization of pregabalin could be obtained in Example 3 relating to the present invention and superior skin permeability of pregabalin from the preparation was confirmed.

INDUSTRIAL APPLICABILITY

The present invention relates to a production method of a pregabalin-containing composition and a pregabalin-containing composition, and is useful in the field of pharmaceutical products.

This application is based on patent application No. 2018-053905 filed in Japan (filing date: Mar. 22, 2018), the contents of which are incorporated in full herein.

The invention claimed is:

1. A pregabalin-containing composition comprising a salt of pregabalin with an acid, and a hydrophilic resin, wherein
   the composition is formulated as a transdermal agent,
   the acid is at least one selected from the group consisting of phytic acid, acrylic acid, polyacrylic acid, poly(p-styrene sulfonic acid), polyvinyl sulfonic acid, polyacrylamide sulfonic acid, alkylsulfuric acid, lactic acid, hydrochloric acid, nitric acid, phosphoric acid, sulfuric acid, hydrobromic acid, hydroiodic acid, and heparin, and
   the hydrophilic resin is at least one selected from the group consisting of polyvinylpyrrolidone, polyethylene glycol, polyvinyl alcohol, cellulose ester, carrageenan, polyacrylic acid, polymethacrylic acid, gelatin, heparin, polyvinyl sulfonic acid, polyacrylamide, and polyacrylamide sulfonic acid.

2. The pregabalin-containing composition according to claim 1, wherein a content of the hydrophilic resin is 0.5-50 parts by mass per 100 parts by mass of the salt contained in the pregabalin-containing composition.

3. The pregabalin-containing composition according to claim 2, wherein the acid is hydrochloric acid.

4. The pregabalin-containing composition according to claim 3, wherein the hydrophilic resin is polyvinylpyrrolidone.

5. The pregabalin-containing composition according to claim 2, wherein the hydrophilic resin is polyvinylpyrrolidone.

6. The pregabalin-containing composition according to claim 1, wherein the acid is an inorganic acid.

7. The pregabalin-containing composition according to claim 6, wherein a content of the hydrophilic resin is 0.5-50 parts by mass per 100 parts by mass of the salt contained in the pregabalin-containing composition.

8. The pregabalin-containing composition according to claim 1, wherein the acid is hydrochloric acid.

9. The pregabalin-containing composition according to claim 8, wherein the hydrophilic resin is polyvinylpyrrolidone.

10. The pregabalin-containing composition according to claim 1, wherein the hydrophilic resin is polyvinylpyrrolidone.

11. A method for producing a pregabalin-containing composition as a transdermal agent, comprising steps of:
    (1) dissolving pregabalin in an aqueous solution of an acid to prepare an aqueous solution of a salt of pregabalin, wherein the acid is at least one selected from the group consisting of phytic acid, acrylic acid, polyacrylic acid, poly(p-styrene sulfonic acid), polyvinyl sulfonic acid, polyacrylamide sulfonic acid, alkylsulfuric acid, lactic acid, hydrochloric acid, nitric acid, phosphoric acid, sulfuric acid, hydrobromic acid, hydroiodic acid, and heparin,
    (2) mixing the aqueous solution of pregabalin salt and a hydrophilic resin to prepare a mixture thereof, wherein the hydrophilic resin is at least one selected from the group consisting of polyvinylpyrrolidone, polyethylene glycol, polyvinyl alcohol, cellulose ester, carrageenan, polyacrylic acid, polymethacrylic acid, gelatin, heparin, polyvinyl sulfonic acid, polyacrylamide, and polyacrylamide sulfonic acid, and
    (3) concentrating the mixture
    wherein the composition is formulated as a transdermal agent.

12. The production method according to claim 11, wherein the acid is an inorganic acid.

13. The production method according to claim 12, wherein a content of the hydrophilic resin is 0.5 50 parts by mass per 100 parts by mass of the salt contained in the mixture.

14. The production method according to claim 11, wherein a content of the hydrophilic resin is 0.5-50 parts by mass per 100 parts by mass of the salt contained in the mixture.

15. The production method according to claim 14, wherein the acid is hydrochloric acid.

16. The production method according to claim 15, wherein the hydrophilic resin is polyvinylpyrrolidone.

17. The production method according to claim 14, wherein the hydrophilic resin is polyvinylpyrrolidone.

18. The production method according to claim 5, wherein the acid is hydrochloric acid.

19. The production method according to claim 18, wherein the hydrophilic resin is polyvinylpyrrolidone.

20. The production method according to claim 5, wherein the hydrophilic resin is polyvinylpyrrolidone.

* * * * *